Figure 1:
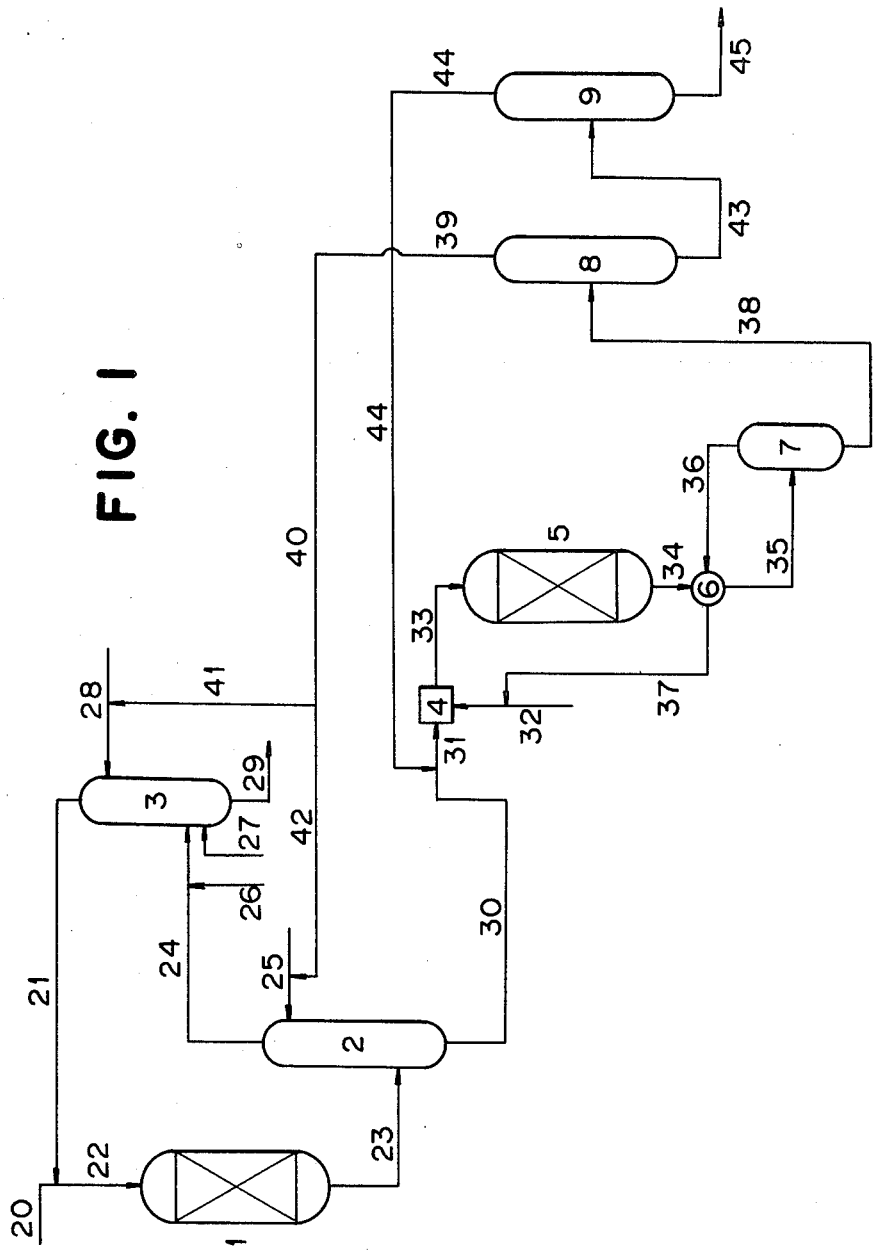

United States Patent [19]

Tahara et al.

[11] 4,453,026

[45] Jun. 5, 1984

[54] PROCESS FOR CONTINUOUSLY PREPARING ETHYLENE GLYCOL

[75] Inventors: Susumu Tahara; Kozo Fujii; Keig Nishihira; Masaoki Matsuda; Katsuhiko Mizutare, all of Ube, Japan

[73] Assignee: Ube Industries, Ltd., Ube, Japan

[21] Appl. No.: 459,424

[22] Filed: Jan. 19, 1983

Related U.S. Application Data

[63] Continuation of Ser. No. 293,704, Aug. 17, 1981, abandoned.

[30] Foreign Application Priority Data

Sep. 2, 1980 [JP] Japan ................. 55-120676
Sep. 2, 1980 [JP] Japan ................. 55-120677
Jan. 22, 1981 [JP] Japan ................. 56-7175

[51] Int. Cl.³ ............... C07C 31/20; C07C 29/136
[52] U.S. Cl. ................. 568/864; 560/204; 260/466
[58] Field of Search ............. 568/864; 560/204

[56] References Cited

U.S. PATENT DOCUMENTS 4,112,245  9/1978  Zehner et al. ................. 568/864
4,229,591 10/1980  Nishimura et al. ............. 560/204

Primary Examiner—J. E. Evans
Attorney, Agent, or Firm—Frishauf, Holtz, Goodman & Woodward

[57] ABSTRACT

There is disclosed a process for continuously preparing ethylene glycol, which comprises (1) a first step of contacting a gas containing carbon monoxide and an ester of nitrous acid with a solid catalyst of platinum group metal series in the gaseous phase thereby to obtain a product containing a diester of oxalic acid, (2) a second step of condensing the product of the first step thereby to separate a non-condensed gas containing nitrogen monoxide formed by the catalytic reaction of the first step from a condensed liquid containing the diester of oxalic acid, (3) a third step of contacting the non-condensed gas of the second step with a gas containing molecular oxygen and an alcohol, and recycling the resulting gas containing an ester of nitrous acid to the first step, (4) a fourth step of contacting the condensed liquid of the second step containing the diester of oxalic acid and hydrogen with a catalyst for hydrogenation in the gaseous phase thereby to obtain a product containing ethylene glycol, (5) a fifth step of distilling the product of the fourth step thereby to distill out the alcohol and to obtain ethylene glycol, and (6) a sixth step of recycling the alcohol of the fifth step as an alcohol source for the third step.

16 Claims, 3 Drawing Figures

FIG. I

PROCESS FOR CONTINUOUSLY PREPARING ETHYLENE GLYCOL

This is a continuation of application Ser. No. 293,704 filed Aug. 17, 1981 abandoned.

The present invention relates to a novel process for preparing ethylene glycol, and particularly to a continuous process for preparing ethylene glycol with use of a diester of oxalic acid obtainable from the gaseous phase reaction of carbon monoxide and an ester of nitrous acid, as the starting material.

Ethylene glycol is useful for various industrial applications, e.g. as starting material for polyester fibers, as starting material for alkyd resins, as an anti-freeze coolant, as a solvent or as a reagent.

There has hitherto been known a process for preparing ethylene glycol by contacting a diester of oxalic acid with hydrogen in the presence of a hydrogenation catalyst in the gaseous phase. Further, as a process for the preparation of a diester of oxalic acid, it is also known to contact carbon monoxide and an ester of nitrous acid in the presence of a platinum group metal catalyst in the gaseous phase.

The present invention provides a continuous process whereby said process for the preparation of a diester of oxalic acid and said process for the preparation of ethylene glycol are ingeniously combined to industrially advantageously prepare ethylene glycol from carbon monoxide, the ester of nitrous acid and hydrogen.

Namely, the present invention is concerned with a process for continuously preparing ethylene glycol, which comprises;

(1) a first step of contacting a gas containing carbon monoxide and an ester of nitrous acid with a solid catalyst of platinum group metal series in the gaseous phase thereby to obtain a product containing a diester of oxalic acid, (2) a second step of condensing the product of the first step thereby to separate a non-condensed gas containing nitrogen monoxide formed by the catalytic reaction of the first step from a condensed liquid containing the diester of oxalic acid, (3) a third step of contacting the non-condensed gas of the second step with a gas containing molecular oxygen and an alcohol, and recycling the resulting gas containing an ester of nitrous acid to the first step, (4) a fourth step of contacting the condensed liquid of the second step containing the diester of oxalic acid and hydrogen with a catalyst for hydrogenation in the gaseous phase thereby to obtain a product containing ethylene glycol, (5) a fifth step of distilling the product of the fourth step thereby to distil out the alcohol and to obtain ethylene glycol, and (6) a sixth step of recycling the alcohol of the fifth step as an alcohol source for the third step.

Now, each step of the present invention will be described.

First step

A gaseous starting material containing carbon monoxide and an ester of nitrous acid, is introduced into a reactor packed with a solid catalyst of platinum group metal series, and thereby a catalytic reaction is carried out in the gaseous phase.

As the reactor, a single tubular or multi-tubular column packed with a catalyst is useful. The contact time of the gaseous stating material with the solid catalyst of a platinum metal series is set to be at most 10 seconds, preferably from 0.2 to 5 seconds.

As the solid catalyst of platinum group metal series, palladium is most useful, but platinum, rhodium, ruthenium, and iridium are also useful. Further, salts of these metals such as nitrates, sulfates, phosphates, halides, acetates, oxalates or benzoates, may be used. These materials are used as carried by an inert carrier such as active carbon, alumina, silica, silica-alumina, diatomaceous earth, pumice, magnesia, zeolite, or Molecular Sieve. The amount to be used, in terms of the platinum group metal, is within a range of from 0.01 to 10% by weight, usually from 0.2 to 2% by weight, relative to the carrier.

The gaseous starting material, i.e. a gas containing carbon monoxide and an ester of nitrous acid may usually be used in a form diluted with an inert gas such as nitrogen or carbon dioxide.

The ester of nitrous acid may preferably be an ester of a saturated monohydric aliphatic or alicyclic alcohol having from 1 to 8 carbon atoms with nitrous acid. As the alcohol component, there may be mentioned, for instance, an aliphatic alcohol such as methanol, ethanol, n-(and iso-)propanol, n-(iso, sec- and tert)butanol, o-(and iso-)amyl alcohol, hexanol, or octanol, and an alicyclic alcohol such as cyclohexanol, or methylcyclohexanol. These alcohols may contain a substituent, such as an alkoxy group, which does not hinder the reaction. Among these, methyl nitrite and ethyl nitrite are most preferably used.

It is necessary to carry out this reaction under such conditions that there is no formation of a liquid phase in the reaction zone. The conditions for no formation of a liquid phase in the reaction zone vary depending upon the reaction temperature, the reaction pressure and the kind and concentration of the ester of nitrous acid used, and therefore can not simply be determined.

However, with respect to the reaction temperature, the reaction proceeds in a sufficiently high speed even at a low temperature, and the lower the reaction temperature is, the less side reactions occur. Accordingly, so long as the desired space time yield can be maintained, the reaction is carried out at a relatively low temperature, i.e. usually from 50° to 200° C., preferably from 80° to 150° C. Further, with respect to the reaction pressure, the reaction is carried out usually under a pressure from the atmospheric pressure to 10 kg/cm$^2$ (gauge pressure), preferably from an atmospheric pressure to 5 kg/cm$^2$ (gauge pressure). However, in some cases, the reaction pressure may be slightly lower than the atmospheric pressure.

The concentration of the ester of nitrous acid in the gaseous starting material may be varied over a wide range. However, in order to attain a satisfactory reaction rate, it is necessary to adjust the concentration to be at least 1% by volume, usually from 5 to 30% by volume.

The concentration of carbon monoxide in the gaseous starting material may be varied over a wide range, and is usually selected within a range of from 10 to 90% by volume.

Second step

The product of the first step is led to a condenser, cooled to a temperature at which the diester of oxalic acid in the product is condensed, and separated into a condensed liquid and a non-condensed gas.

The condensed liquid thus separated contains the diester of nitrous acid as a main component. However, the diester of carbonic acid and the ester of formic acid which have been formed as by-products in the first step are also contained therein in small amounts. On the other hand, the non-condensed gas contains non-reacted carbon monoxide, an ester of nitrous acid and the like, in addition to the nitrogen monoxide formed by the catalytic reaction of the first step.

Further, during this step, a part of the diester of oxalic acid is carried by the non-condensed gas, and then hydrolized by water formed during the regeneration of nitrogen monoxide into the ester of nitrous acid in the subsequent third step, and it is possible that the resulting oxalic acid accumulates within the gas recycling system. Furthermore, when the intended product is the one having a relatively high melting point, such as dimethyl oxalate, it is possible that the intended product solidifies and deposits on the wall of the condenser and finally plugs the condenser.

In order to solve these problems, it is possible to employ a method wherein the product of the first step is cooled for condensation at a temperature of at most the boiling point of an alcohol while contacting it with the alcohol. For instance, when the intended product is dimethyl oxalate, it is preferred that the cooling and condensation are carried out at a temperature of from 30° to 60° C. while supplying from 0.01 to 0.1 part by volume of methanol, relative to 100 parts by volume of the product to be treated, along the wall surface of the condenser.

Third step

The non-condensed gas separated in the second step is led to a regeneration column and contacted with a gas containing molecular oxygen and an alcohol thereby to regenerate nitrogen monoxide in the gas into an ester of nitrous acid.

As the regeneration column for this step, a usual gas-liquid contact apparatus such as a packed column, a bubble column, a spray column, or a multi-stage column, may be employed. The alcohol to be used, is preferably the same alcohol as the alcohol component which constitutes said ester of nitrous acid.

The non-condensed gas to be contacted with the alcohol and the gas containing molecular oxygen, may be introduced into the regeneration column individually or in a mixed state.

In the regeneration column, a part of nitrogen monoxide is oxidized to nitrogen dioxide and at the same time, these substances are allowed to be absorbed and react with an alcohol and thereby to be regenerated as an ester of nitrous acid.

In this step, it is preferred to control the concentration of nitrogen monoxide in the gas withdrawn from the regeneration column to be within a range of from 2 to 7% by volume, and to maintain the gas to contain as little nitrogen dioxide and oxygen as possible, and preferably no nitrogen dioxide and oxygen. Namely, if the concentration of nitrogen monoxide in the regenerated gas is greater than the above mentioned upper limit, the reaction rate for the formation of the diester of oxalic acid is decreased and the yield is lowered, when said gas is recycled for use in the reactor of the first step. On the other hand, if said concentration is lower than the above-mentioned lower limit, the amounts of nitrogen dioxide and oxygen will be increased in the regenerated gas, and they will be factors for substantial degradation of the activity of the solid catalyst of platinum group metal series and for an increase in the formation of carbon dioxide as a by-product.

Accordingly, it is preferred that from 0.08 to 0.2 mole, as calculated as oxygen, of the gas containing molecular oxygen, relative to one mole of nitrogen monoxide in the gas introduced to the regeneration column, is supplied and these gases are contacted with the alcohol at a temperature of at most the boiling point of the alcohol thus used. The contact time is preferably from 0.5 to 20 seconds. Further, the alcohol is used in such an amount as to be sufficient for completely absorbing and reacting the resulting nitrogen dioxide and an almost equimolar amount of nitrogen monoxide, and usually, from 2 to 5 parts by volume of the alcohol is preferably used relative to one part by volume of nitrogen monoxide in the gas introduced into the regeneration column.

Further, a loss of a nitrogen component may be complemented by supplying the ester of nitrous acid to the reactor of the first step, or by introducing a nitrogen oxide such as nitrogen monoxide, nitrogen dioxide, dinitrogen trioxide, or dinitrogen tetraoxide or nitric acid into the regeneration column of the third step.

Further, in case the content of nitrogen monoxide in the non-condensed gas in the second step is great, and if the ester of nitrous acid is obtainable in an excess amount during the regeneration of the nitrogen monoxide into the ester of nitrous acid in the third step, the entire amount of the non-condensed gas need not be led to the regeneration column and a part thereof may be directly recycled to the reactor of the first step.

The gas containing the ester of nitrous acid and withdrawn from the regeneration column, is recycled to the reactor of the first step. Further, this regenerated gas may be mixed with another starting material, i.e. carbon monoxide, and then the mixture may be supplied to the reactor.

When the regenerated ester of nitrous acid is an ester of an alcohol having at least 4 carbon atoms, such as n-butyl nitrite, or n-amyl nitrite, it forms an azeotropic mixture with water formed as a by-product by the regeneration reaction and consequently, water is contained in the regenerated gas. Accordingly, if this gas is supplied as such to the reactor of the first step, the water hinders the reaction for the formation of the diester of oxalic acid. Therefore, it is desirable that water in the gas is removed by an operation such as distillation before the gas is recycled to the reactor. On the other hand, when the regenerated ester of nitrous acid is methyl nitrite, ethyl nitrite, n-propyl nitrite, or isopropyl nitrite, it does not form an azeotropic mixture with water formed as a by-product by the regeneration reaction, and accordingly, the regenerated gas contains no water and may therefore be recycled to the reactor as it is.

The liquid withdrawn from the regeneration column is an alcohol solution containing water formed as a by-product by the regeneration reaction. This may be refined by distillation, extraction or other operation to such an extent that the water content in the alcohol becomes at most 5% by volume, preferably at most 2% by volume, and may then be reused as an alcohol source for the third step, and in a proper case, as an alcohol source for the second step.

Fourth step

The condensed liquid containing the diester of oxalic acid, which was obtained by the second step and hydrogen, and optionally the glycolic acid from the fifth step mentioned below, are led to a reactor packed with a catalyst for hydrogenation and catalytically reacted in the gaseous phase.

As the reactor, a fixed bed or a fluidized bed is useful. The contact time of the gaseous starting material and the catalyst for hydrogenation is set to be at most 5 seconds, preferably 0.2 to 2 seconds.

The catalyst for hydrogenation may be of a known type such as copper chromite, zinc copper chromite, barium chromite, ammonium copper chromate, zinc chromate, Raney nickel, manganese chromite or magnesium chromite. They may be used by themselves or in such a form as carried by an inert carrier such as active carbon, alumina, silica, diatomaceous earth, pumice, zeolite, or Molecular Sieve.

Hydrogen is preferably used in an amount in excess of the stoichiometric amount required to convert the diester of oxalic acid into ethylene glycol and an alcohol corresponding to the ester residue of the diester of oxalic acid.

The reaction temperature is usually from 150° to 300° C., preferably from 180° to 230° C. The reaction pressure is at least the atmospheric pressure, preferably from 10 to 40 atmospheres.

The major proportion of the reaction product in this step consists of ethylene glycol and the alcohol corresponding to the ester residue of the diester of oxalic acid. However, a small amount of an ester of glycolic acid produced by partial hydrogenation of the diester of oxalic acid, is also contained in the product.

In the meantime, it may be preferred that the condensed liquid containing the diester of oxalic acid of the second step is preliminarily let to a distillation column, before it is contacted with hydrogen in the gaseous phase to carry out the catalytic reaction of this step (fourth step), to thereby obtain the diester of oxalic acid as the distillation residue which is then contacted with hydrogen in the gaseous phase according to the procedure of this step (fourth step). In this case, the major part of the components other than the diester of oxalic acid is removed by the preliminary distillation operation. Thus, the process using the preliminary distillation column has an industrial advantage.

In the distillate from the preliminary distillation column, there are contained, in addition to the alcohol, a diester of carbonic acid formed as a by-product by the catalytic reaction in the first step, and a small amount of an ester of formic acid.

This distillate is contacted with steam, whereby the diester of carbonic acid and the ester of formic acid in the distillate are hydrolized to the alcohol and carbon dioxide.

The obtained alcohol may be recycled as an alcohol source for the third step. Further, in the case where in the second step, the condensation is carried out while contacting the non-condensed gas with an alcohol, the obtained alcohol may be recycled as the alcohol source therefor.

This hydrolysis can readily be carried out by a gas phase reaction in the presence of an alumina catalyst such as, e.g., Neobead P (trade name) made by Mizusawa Kagaku Co., at a temperature of from 150° to 250° C.

Further, the distillation column or the hydrolysis column used in this step, may be a usual apparatus such as a packed column, a multi-stage column, and a forced agitation type thin film column.

Fifth and sixth steps

The product of the fourth step is led to a distillation column and distilled by a usual operation, whereby the intended ethylene glycol is obtained as the distillation residue while the alcohol corresponding to the ester residue of the diester of oxalic acid is distilled off.

The distilled alcohol is recycled as a part of the alcohol source for the regeneration column of the third step. Further, in the case where, in the second step, the condensation is carried out while contacting the non-condensed gas with an alcohol, it may be recycled as a part of the alcohol source for that step.

The distillation residue contains, in addition to the intended ethylene glycol, a small amount of an ester of glycolic acid. However, it is possible to obtain refined ethylene glycol by subjecting the distillation residue to distillation to distil off the ester of glycolic acid. Further, the ester of glycolic acid is hydrogenated into ethylene glycol in the same manner as the diester of oxalic acid, under the conditions for hydrogenation in the fourth step, and therefore, said ester of glycolic acid thus distilled, may be recycled to the fourth step.

If necessary, the distillation residue obtained by the distillation of the ester of glycolic acid is subjected further to distillation so that ethylene glycol of high purity may be obtained.

The distillation columns in the fifth and sixth steps, may be of a usual type, such as a multi-stage column, a packed column or a forced agitation type thin film column.

The process may be carried out so that, before the product of the fourth step is led to the distillation column, the product is separated into a non-condensed gas containing hydrogen and a condensed liquid containing ethylene glycol, and the non-condensed gas is recycled as a hydrogen source of the fourth step. The separation of the non-condensed gas from the condensed liquid is carried out by introducing the product of the fourth step into a condenser and cooling the product to a temperature at which the ethylene glycol in the product is condensed.

Now, the process of this invention will be described in detail in accordance with the flowsheet diagram illustrating an embodiment of the present invention. In the FIG. 1, 1 and 5 are reactors, 2 and 7 are condensers, 3 is a regeneration column, 8 and 9 are distillation columns, 4 is a heater, 6 is a heat exchanger, and 20 to 45 are conduits.

Carbon monoxide from conduit 20 and a gas containing an ester of nitrous acid, nitrogen monoxide, etc. from conduit 21, are compressed by a gas recycling device (not shown) and introduced via conduit 22 into a reactor 1 packed with a solid catalyst of platinum group metal series. In the reactor 1, the catalytic reaction is carried out in the gaseous phase. The gaseous reaction product passed through the catalyst layer is withdrawn from the bottom and led to a condenser 2 via conduit 23.

In condenser 2, the gaseous reaction product is condensed while, if desired being contacted with an alcohol supplied from conduit 25. The condensed liquid containing a diester of oxalic acid as the major component is withdrawn through conduit 30. On the other hand, the non-condensed gas containing non-reacted carbon monoxide and ester of nitrous acid, and nitrogen monoxide formed as a by-product, is led to the bottom of a regeneration column 3 via conduit 24.

In regeneration column 3, the non-condensed gas is counter-currently contacted and reacted with a gas containing molecular oxygen supplied to the bottom via conduit 27 and an alcohol supplied to the top via conduit 28, whereby an ester of nitrous acid is formed. In this regeneration column 3, the oxidation reaction of nitrogen monoxide to nitrogen dioxide, is followed by an absorption reaction thereof into the alcohol. Further, in case a nitrogen source required for the formation of the ester of nitrous acid is lacking, a nitrogen oxide may be supplied from conduit 26.

The gas formed in the regeneration column 3 and containing the ester of nitrous acid thereby formed, is recycled to the reactor 1 via conduits 21 and 22, together with carbon monoxide supplied afresh from conduit 20. On the other hand, water formed as a by-product in the regeneration column 3 is withdrawn from the bottom via conduit 29 in a form of an aqueous solution of an alcohol. This aqueous alcohol solution is subjected to an operation such as distillation to remove the water in the solution, and then may be reused as an alcohol source to be supplied to the regeneration column 3 or the condenser 2 via said conduit 28 or 25.

The condensed liquid containing the diester of oxalic acid, which was obtained from condenser 2, is passed through a conduit 30, mixed with an ester of glycolic acid from conduit 44 as the case requires, pressurized to a desired level by a pressurizing pump (not shown), then passed through conduit 31, led to heater 4 and contacted with hydrogen from conduit 32. The gaseous mixture thus obtained is passed through conduit 33, led to reactor 5 packed with a catalyst for hydrogenation, and subjected to catalytic reaction in the gaseous phase. The gaseous reaction product is withdrawn through conduit 34, cooled by heat exchanger 6 and led to condenser 7 via conduit 35.

In condenser 7, the gaseous reaction product is condensed, and the condensed liquid containing ethylene glycol as the major component is led to distillation column 8 via conduit 38. On the other hand, the non-condensed gas containing hydrogen as the major component, is withdrawn through conduit 36, pressurized to a desired level by a pressurizing pump (not shown), then heated by heat exchanger 6, passed through conduit 37, mixed with hydrogen from conduit 32, and led to heater 4.

In the distillation column 8, the alcohol is distilled off through conduit 39, and this alcohol is recycled as an alcohol source to be supplied to regeneration column 3 via conduits 40, 41 and 28. Further, a part of this alcohol may be reused as an alcohol source to be supplied to condenser 2 via conduits 42 and 25, as the case requires. The distillation residue is withdrawn through conduit 43 and led to distillation column 9.

The ester of glycolic acid as a by-product distilled at the distillation column 9, is passed through conduit 44, and mixed with the diester of oxalic acid from conduit 30 as the case requires, and then may be led to heater 4 via conduit 31. On the other hand, the intended ethylene glycol as the distillation residue, is withdrawn through a conduit 45.

Figure 2:
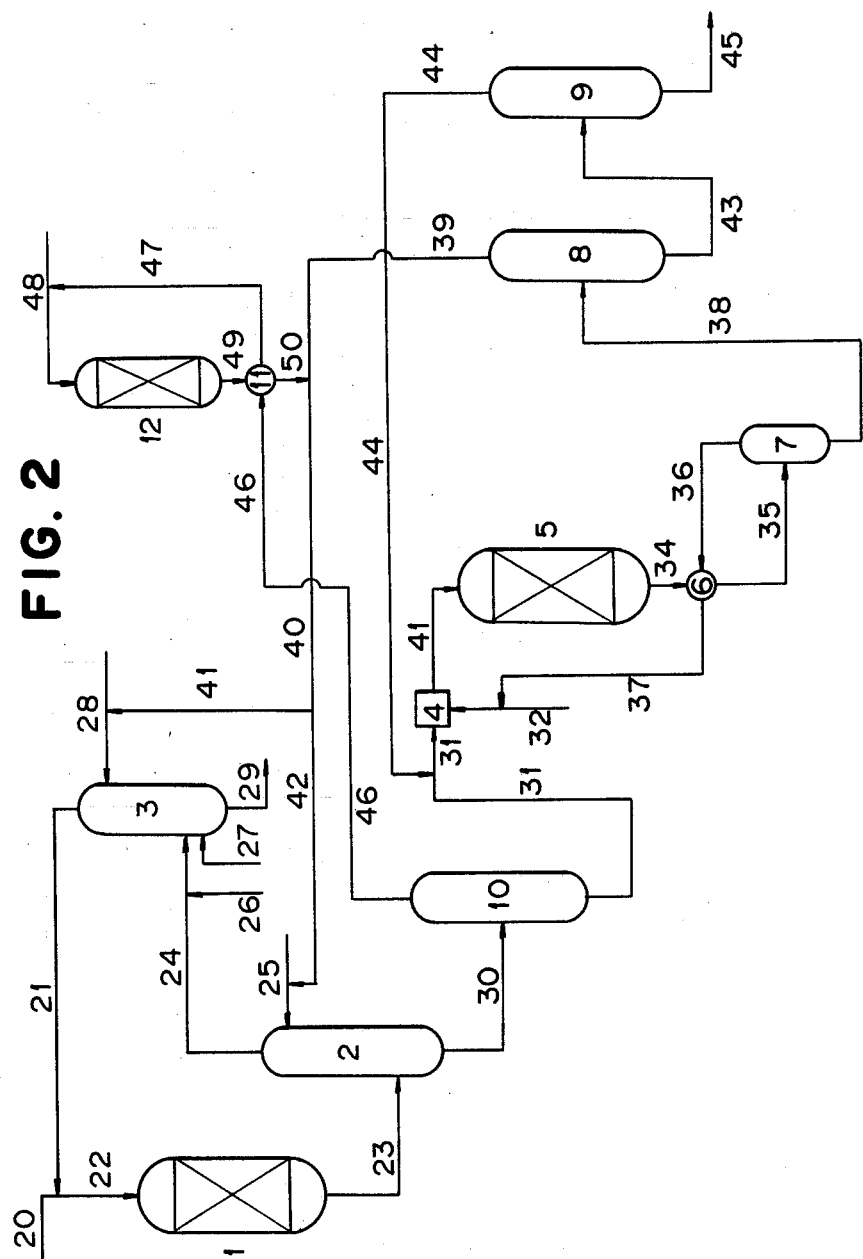

Next, another embodiment of this invention will be described in detail in accordance with the flowsheet diagram as shown in FIG. 2. In this embodiment, the alcohol, the diester of carbonic acid as a by-product, and so on are preliminarily distilled out from the condensed liquid containing the diester of oxalic acid before the condensed liquid is led to heater 4 through conduit 30. In FIG. 2, 1 to 45 have the same meanings as in FIG. 1, and 10 is a distillation column; 11 is a heat exchanger; 12 is a hydrolysis column; and 46 to 50 are conduits.

In the distillation column 10, the alcohol, an diester of carbonic acid as a by-product, etc. are distilled off, and the diester of oxalic acid is withdrawn via conduit 31.

The distillate is passed through conduit 46, heated by heat exchanger 11, then passed through conduit 47, mixed with steam from conduit 48 and led to hydrolysis column 12.

In hydrolysis column 12, the diester of carbonic acid and an ester of formic acid in the gas are hydrolyzed by the action of an alumina series catalyst into an alcohol and carbon dioxide. The gaseous alcohol thereby formed, is passed through conduit 49, cooled by heat exchanger 11, and then freed from carbon dioxide in the gas and at the same time condensed, in a condenser (not shown). Then, this alcohol is passed through conduits 50, 40 and 41 and recycled as an alcohol source to be supplied to regeneration column 3 via conduit 28. Further, a part of this alcohol, may be reused as an alcohol source to be supplied to condenser 2 via conduits 42 and 25, as the case requires.

Figure 3:
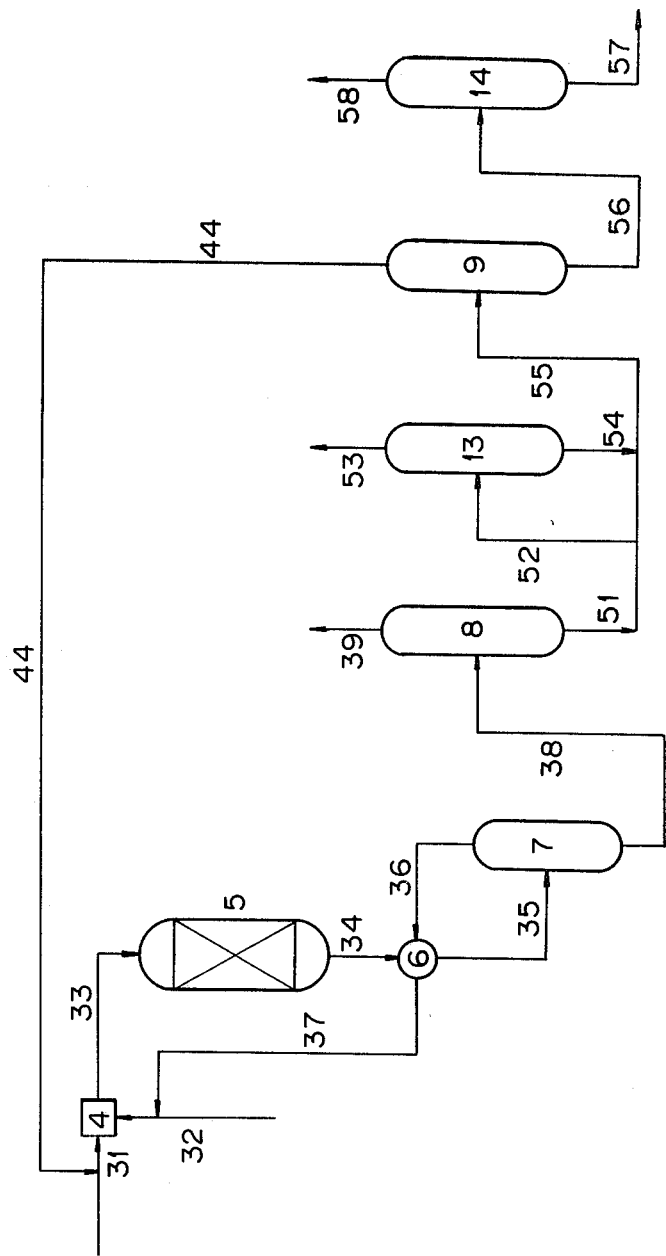

Further, by way of the flowsheet diagram as shown in FIG. 3., still another preferred embodiment of this invention will be described in detail, in which ethylene glycol is obtained by distilling off the alcohol and the ester of glycolic acid formed as a by-product from the condensed liquid obtained in condenser 7 and containing ethylene glycol as the major component. In FIG. 3, 4 to 44 have the same meanings as in FIGS. 1 and 2, and 13 and 14 are distillation columns; and 51 to 59 are conduits.

In distillation column 8, the alcohol corresponding to the ester residue of the diester of oxalic acid formed as a by-product, is distilled out through conduit 39. The distillation residue is withdrawn through conduits 51 and 55 and led to distillation column 9.

In the distillation column 9, an ester of glycolic acid formed as a by-product, is distilled out through conduit 44 and mixed with the diester of oxalic acid from conduit 31.

Further, the distillation residue of distillation column 8, usually contains light-boiling substances such as ethanol and water. Accordingly, although the distillation residue of distillation column 8 may be led directly to distillation column 9 as mentioned above, it is preferred to provide a route in which said residue may be led to distillation column 13 via conduit 52, and said light-boiling substances may be distilled out through conduit 53, and the distillation residue thereby obtained may be led to distillation column 9 via conduits 54 and 55.

If desired, the distillation residue of distillation column 9 may be led to distillation column 14 via conduit 56 to obtain the intended ethylene glycol of high purity through conduit 58. In this case, the high boiling distillation residue is discharged via conduit 57 out of the system.

Now, the present invention will be explained in more detail with reference to the following Examples which should not be construed to limit the present invention.

EXAMPLE 1

In the tubes of a stainless multi-tubular reactor A, which has 6 tubes having an inside diameter of 36.7 mm and a height of 550 mm, there was packed 3 kg (3 liters) of a γ-alumina catalyst in a form of pellets having a diameter of 5 mm and a height of 3 mm and carrying 0.5% by weight of palladium.

A gaseous mixture of carbon monoxide and the regenerated gas from the regeneration column mentioned below (pressure: 0.2 kg/cm$^2$G, composition: 22.0% by volume of carbon monoxide, 9.1% by volume of methyl nitrite, 3.1% by volume of nitrogen monoxide, 9.4% by volume of methanol, 8.5% by volume of carbon dioxide and 47.0% by volume of nitrogen) was preheated to about 90° C. by a heat exchanger, and then introduced from the top of this catalyst layer at a rate of 12.0 Nm$^3$/hr by a diaphragm gas-recycling pump, and the temperature of the catalyst layer was maintained at 104° to 117° C. by circulating hot water to the shell side of the reactor.

The gas passed through the catalyst layer was led to the bottom of a Rasching ring packed gas-liquid contact condenser A having an inside diameter of 158 mm and a height of 1,400 mm, and from the top of the condenser, methanol was introduced at a rate of 5.6 liters/hr., whereby the countercurrent contact was carried out at a temperature of about 35° C. (i.e. 30° C. at the top of the condenser and 40° C. at the bottom of the condenser). From the bottom of the condenser, there was obtained 2.8 kg/hr. of a condensed liquid (composition: 46.6% by weight of dimethyl oxalate, 4.9% by weight of dimethyl carbonate, 0.03% by weight of methyl formate and 48.0% by weight of methanol). On the other hand, from the top of the condenser, 13.6 Nm$^3$/hr. of a non-condensed gas (composition: 15.4% by volume of carbon monoxide, 3.9% by volume of methyl nitrite, 6.8% by volume of nitrogen monoxide, 24.2% by volume of methanol, 7.6% by volume of carbon dioxide and 41.4% by volume of nitrogen) was obtained.

To this non-condensed gas, 140 liters/hr. of oxygen and 9 liters/hr. of nitrogen monoxide were mixed (the molar ratio of oxygen to nitrogen monoxide in the gas being 0.15) and the mixture was led to the bottom of the gas-liquid contact type regeneration column having an inside diameter of 158 mm and a height of 1,400 mm. From the top of the column, methanol (including the methanol recycled from the regeneration column) was supplied at a rate of 40 liters/hr. (2.2 liters/hr. of which was the one supplied from the distillation column A mentioned below). The countercurrent contact was carried out at a temperature of about 35° C. (i.e.30° C. at the top of the column and 40° C. at the bottom of the column), whereby nitrogen oxide in the gas was regenerated into methyl nitrite. To 13.6 Nm$^3$/hr. of the regenerated gas from the regeneration column (composition: 15.4% by volume of carbon monoxide, 8.0% by volume of methyl nitrite, 2.8% by volume of nitrogen monoxide, 24.2% by volume of methanol, 7.6% by volume of carbon dioxide and 41.3% by volume of nitrogen), there was added 550 liters/hr. of carbon monoxide, and the mixture was supplied to and compressed by said gas recycling pump. The discharged gas was cooled to 20° C. to remove condensed methanol, and then led to the reactor A.

On the other hand, 1.4 liters/hr. of an aqueous methanol solution containing 20.0% by weight of water, withdrawn from the regeneration column, was subjected to distillation to remove water and then reused as a methanol source for said column.

Mixed with 2.8 kg/hr. of the condensed liquid withdrawn from said condenser A was 0.05 kg/hr. of methyl glycolate obtained from the distillation column B mentioned below. The mixture was pressurized to 30 kg/cm$^2$G, mixed with 29.8 Nm$^3$/hr. of a gas having the same pressure and composed of 74.0% by volume of hydrogen, and 25.2% by volume of nitrogen, and heated to about 200° C. The gaseous mixture thereby obtained was supplied to the reactor B having an inside diameter of 42.6 mm and a height of 2500 mm (packed with 3.0 liters of Cu-Cr-Ba series ST-203 catalyst made by Sakai Kagaku Co.).

The gas passed through the catalyst layer, was led to the condenser B having an inside diameter of 53.5 mm and a height of 1500 mm, and cooled to about 40° C. From the bottom, there was obtained 2.85 kg/hr. of a condensed liquid (composition: 22.8% by weight of ethylene glycol, 75.4% by weight of methanol, and 1.7% by weight of methyl glycolate). On the other hand, 28.6 Nm$^3$/hr. of the non-condensed gas withdrawn from the top (composition: 73.8% by volume of hydrogen, and 26.2% by volume of nitrogen) was recycled as said hydrogen source.

To the distillation column A having an inside diameter of 30 mm and a height of 3000 mm, 2.85 kg/hr. of the condensed liquid obtained from the condenser B was led, and distillation was carried out at a temperature of 65° C. at the top and 158° C. at the bottom. The methanol distilled from the top was recycled to said regeneration column at a rate of 2.7 liter/hr. On the other hand, 0.71 kg/hr. of the distillation residue obtained from the bottom (composition: 91.6% by weight of ethylene glycol, and 7.0% by weight of methyl glycolate), was led to a distillation column B having an inside diameter of 30 mm and a height of 3000 mm, and distilled at a temperature of 95° C. at the top and 158° C. at the bottom. Recycled to said reactor B was 0.5 kg/hr. of methyl glycolate distilled from the top. On the other hand, from the bottom, there was obtained 0.70 kg/hr. of ethylene glycol having a purity of 98.5% by weight, as the distillation residue.

EXAMPLE 2

In the tubes of a stainless multi-tubular reactor A, which has 6 tubes having an inside diameter of 36.7 mm and a height of 550 mm, there was packed 2.5 kg (2.5 liters) of γ-alumina catalyst in a form of pellets having a diameter of 5 mm and a height of 3 mm and carrying 0.5% by weight of palladium.

A gaseous mixture compressed under a pressure of 1.8 kg/cm$^2$G and composed of carbon monoxide and the regenerated gas from the regeneration column mentioned below (composition: 20.0% by volume of carbon monoxide, 15.1% by volume of methyl nitrite, 3.1% by volume of nitrogen monoxide, 13.2% by volume of methanol, 2.0% by volume of carbon dioxide and 46.9% by volume of nitrogen) was preheated to about 90° C. by a heat exchanger, and then introduced from the top of this catalyst layer at a rate of 5.4 Nm$^3$/hr. by a diaphragm gas-recycling pump, and the temperature of the catalyst layer was maintained at 110° C. by circulating hot water to the shell side of the reactor.

The gas passed through the catalyst layer was led to the bottom of a Rasching ring packed gas-liquid contact type condenser A having an inside diameter of 158 mm and a height of 1,400 mm, and from the top of the condenser, methanol was introduced at a rate of 1.3 liters/hr., whereby the countercurrent contact was carried out at a temperature of 40° C. at the top and 43° C. at the bottom. From the bottom of the condenser, there was obtained 2.2 kg/hr. of a condensed liquid (composition: 48.0% by weight of dimethyl oxalate, 1.5% by weight of dimethyl carbonate, 0.3% by weight of methyl formate and 48.0% by weight of methanol). On the other hand, from the top of the condenser 5.0 Nm$^3$/hr. of a non-condensed gas (composition: 13.3% by volume of carbon monoxide, 7.4% by volume of methyl nitrite, 11.9% by volume of nitrogen monoxide, 14.2% by volume of methanol, 2.4% by volume of carbon dioxide and 50.9% by volume of nitrogen) was obtained.

To this non-condensed gas, 104.0 liters/hr. of oxygen was mixed (the molar ratio of oxygen to nitrogen monoxide in the gas being 0.18) and the mixture was led to the bottom of the gas-liquid contact type regeneration column having an inner diameter of 158 mm and a height of 1,400 mm. From the top of the column, methanol was supplied at a rate of 5.0 liters/hr. (2.0 liters/hr. of which was the one supplied from the distillation column A mentioned below. The countercurrent contact was carried out at a temperature of 40° C. at the top and 42° C. at the bottom, whereby nitrogen oxide in the gas was regenerated into methyl nitrite. The regenerated gas from the regeneration column (composition: 13.0% by volume of carbon monoxide, 16.3% by volume of methyl nitrite, 3.4% by volume of nitrogen monoxide, 14.7% by volume of methanol, 2.3% by volume of carbon dioxide and 50.0% by volume of nitrogen), was supplied to d compressed by said recycling pump at a rate of 5.1 Nm$^3$/hr. To 4.7 Nm$^3$/hr. of the discharged gas, there was added 0.7 Nm$^3$/hr. of a gaseous mixture containing 66.8% by volume of carbon monoxide, 6.3% by volume of methyl nitrite, 1.3% by volume of methanol, and 25.6% by volume of nitrogen. The mixture was led to the reactor A. On the other hand, 4.15 liters/hr. of an aqueous methanol solution containing 94.5% by weight of methanol, withdrawn from the regeneration column, was subjected to distillation to remove water and then reused as a methanol source for said column.

Mixed with 2.2 kg/hr. of the condensed liquid withdrawn from said condenser A was 72.5 g/hr. of methyl glycolate obtained from the distillation column B mentioned below. The mixture was pressurized to 30 kg/cm$^2$G, mixed with 10.0 Nm$^3$/hr. of a gas having the same pressure and composed of 83.2% by volume of hydrogen, and 14.0% by volume of nitrogen, and heated to about 200° C. The gaseous mixture thereby obtained was supplied to the reactor B having an inside diameter of 42.6 mm and a height of 2500 mm (packed with 3.0 liters of Cu-Cr-Ba series ST-203 catalyst made by Sakai Kagaku Co.).

The gas passed through the catalyst layer, was led to the condenser B having an inside diameter of 53.5 mm and a height of 1500 mm, and cooled to about 40° C. From the bottom, there was obtained 2.3 kg/hr. of a condensed liquid (composition: 23.1% by weight of ethylene glycol, 72.5% by weight of methanol, and 3.2% by weight of methyl glycolate). On the other hand, 9.2 Nm$^3$/hr. of the non-condensed gas withdrawn from the top (composition: 83.7% by volume of hydrogen, and 15.5% by volume of nitrogen) was recycled as said hydrogen source.

To the distillation column A having an inside diameter of 30 mm and a height of 3000 mm 2.3 kg/hr. of the condensed liquid obtained from the condenser B was led, and distillation was carried out at a temperature of 65° C. at the top and 158° C. at the bottom. The methanol distilled from the top was recycled to said regeneration column at a rate of 2.0 liters/hr. On the other hand, 0.59 kg/hr. of the distillation residue obtained from the bottom (composition: 84.7% by weight of ethylene glycol, and 12.2% by weight of methyl glycolate), was led to a distillation column B having an inside diameter of 30 mm and a height of 3000 mm, and distilled at a temperature of 95° C. at the top and 158° C. at the bottom. Recycled to said reactor B was 72.5 g./hr. of methyl glycolate distilled from the top. On the other hand, from the bottom, there was obtained 0.51 k/hr. of ethylene glycol having a purity of 98.1% by weight, as the distillation residue.

EXAMPLE 3

In the tubes of a stainless multi-tubular reactor A, which has 6 tubes having an inside diameter of 36.7 mm and a height of 550 mm, there was packed 3 kg (3 liters) of a γ-alumina catalyst in a form of pellets having a diameter of 5 mm and a height of 3 mm and carrying 0.5% by weight of palladium.

A gaseous mixture of carbon monoxide and the regenerated gas from the regeneration column mentioned below [pressure: 0.2 kg/cm$^2$ (gauge pressure) composition: 22.0% by volume of carbon monoxide, 9.1% by volume of methyl nitrite, 3.1% by volume of nitrogen monoxide, 9.4% by volume of methanol, 8.5% by volume of carbon dioxide and 47.0% by volume of nitrogen] was preheated to about 90° C. by a heat exchanger, and then introduced from the top of this catalyst layer at a rate of 12.0 Nm$^3$/hr. by a diaphragm gas-recycling pump, and the temperature of the catalyst layer was maintained at 104° to 117° C. by circulating hot water to the shell side of the reactor.

The gas passed through the catalyst layer was led to the bottom of a Rasching ring packed gas-liquid contact type condenser A of having an inside diameter of 158 mm and a height of 1,400 mm, and from the top of the condenser, methanol was introduced at a rate of 5.6 liters/hr., whereby the countercurrent contact was carried out at a temperature of about 35° C. (i.e. 30° C. at the top of the condenser and 40° C. at the bottom of the condenser). From the bottom of the condenser, there was obtained 2.8 kg/hr. of a condensed liquid (composition: 46.6% by weight of dimethyl oxalate, 4.9% by weight of dimethyl carbonate, 0.03% by weight of methyl formate and 48.0% by weight of methanol). On the other hand, from the top of the condenser, 13.6 Nm$^3$/hr. of a non-condensed gas (composition: 15.4% by volume of carbon monoxide, 3.9% by volume of methyl nitrite, 6.8% by volume of nitrogen monoxide, 24.2% by volume of methanol, 7.6% by volume of carbon dioxide and 41.4% by volume of nitrogen) was obtained.

To this non-condensed gas, 140 liters/hr. of oxygen and 9 liters/hr. of nitrogen monoxide were mixed (the molar ratio of oxygen to nitrogen monoxide in the gas being 0.15) and the mixture was led to the bottom of the gas-liquid contact type regeneration column having an inside diameter of 158 mm and a height of 1,400 mm. From the top of the column, methanol including the methanol recycled from the regeneration column was supplied at a rate of 40 liters/hr. (0.7 liter/hr. of which was the one supplied from the distillation column B mentioned below and 1.77 l./hr. of which was the one supplied from the hydrolysis column mentioned below. The countercurrent contact was carried out at a temperature of about 35° C. (i.e. 30° C. at the top of the column and 40° C. at the bottom of the column), whereby nitrogen oxide in the gas was regenerated into methyl nitrite. To 14.2 Nm³/hr. of the regenerated gas from the regeneration column (composition: 15.4% by volume of carbon monoxide, 8.0% by volume of methyl nitrite, 2.8% by volume of nitrogen monoxide, 24.2% by volume of methanol, 7.6% by volume of carbon dioxide and 41.3% by volume of nitrogen), there was added 550 liters/hr. of carbon monoxide, and the mixture was supplied to and compressed by said gas recycling pump. The discharged gas was cooled to 20° C. to remove condensed methanol, and then led to the reactor A.

On the other hand, 1.2 liters/hr. of an aqueous methanol solution containing 20.0% by weight of water, withdrawn from the regeneration column, was subjected to distillation to remove water and then reused as a methanol source for said column.

To a distillation column A having an inside diameter of 30 mm and a height of 3,000 mm, 2.8 kg/hr. of the condensed liquid withdrawn from said condenser A was introduced and distilled at a temperature of 63° C. at the top and 166° C. at the bottom. From the bottom, 1.32 kg/hr. of a dimethyl oxalate liquid having a purity of 98.0% by weight was obtained. On the other hand, 0.96 Nm³/hr. of a gaseous distillate composed of 96.7% by volume of methanol, 3.2% by volume of dimethyl carbonate and 0.02% by volume of methyl formate, was obtained.

This gaseous distillate was led to a hydrolysis column having an inside diameter of 28.4 mm and a height of 1,000 mm [packed with 500 ml. of Neobead P (trade name) made by Mizusawa Kagaku Co.] and contacted with 50 g./hr. of steam at about 200° C., whereby dimethyl carbonate and methyl formate in the gas were hydrolized and 1.77 liters/hr. of methanol was obtained and recycled to the abovementioned regeneration column.

Mixed with 1.32 kg./hr. of dimethyl oxalate obtained from said distillation column A was 0.05 kg./hr. of methyl glycolate obtained from the distillation column C mentioned below. The mixture was pressurized to 30 kg./cm²G., mixed with a gas having the same pressure and composed of 57.5% by volume of hydrogen, and 42.5% by volume of nitrogen, and heated to about 200° C. The gaseous mixture thereby obtained was supplied to a reactor B having an inside diameter of 42.6 mm and a height of 2500 mm (packed with 3.0 liters of Cu-Cr-Ba series ST-203 catalyst made by Sakai Kagaku Co.) at a rate of 30 Nm³/hr.

The gas passed through the catalyst layer, was led to a condenser B having an inside diameter of 53.5 mm and a height of 1500 mm, and cooled to about 40° C. From the bottom, there was obtained 1.5 kg./hr. of a condensed liquid (composition: 43.9% by weight of ethylene glycol, 47.4% by weight of methanol, and 6.4% by weight of methyl glycolate). On the other hand, 28.7 Nm³/hr. of the non-condensed gas withdrawn from the top (composition: 73.8% by volume of hydrogen, and 26.2% by volume of nitrogen) was recycled as said hydrogen source.

To the distillation column B having an inside diameter of 30 mm and a height of 3000 mm, 1.5 kg./hr. of the condensed liquid obtained from the condenser B was led, and distillation was carried out at a temperature of 65° C. at the top and 158° C. at the bottom. The methanol distilled from the top was recycled to said regeneration column at a rate of 0.7 liter/hr. On the other hand, 0.79 kg./hr. of the distillation residue obtained from the bottom (composition: 83.6% by weight of ethylene glycol, and 12.2% by weight of methyl glycolate), was led to a distillation column C having an inside diameter of 30 mm and a height of 3000 mm, and distilled at a temperature of 95° C. at the top and 158° C. at the bottom. Recycled to said reactor B was 0.05 kg./hr. of methyl glycolate distilled from the top. On the other hand, from the bottom, there was obtained 0.67 kg./hr. of ethylene glycol having a purity of 98.0% by weight, as the distillation residue.

EXAMPLE 4

In the tubes of a stainless multi-tubular reactor A, which has 6 tubes having an inside diameter of 36.7 mm and a height of 550 mm, there was packed 2.5 kg. (2.5 liters) of a γ-alumina catalyst in a form of pellets having a diameter of 5 mm and a height of 3 mm and carrying 0.5% by weight of palladium.

A gaseous starting material compressed under a pressure of 1.8 kg./cm² (gauge presure) (composition: 20.0% by volume of carbon monoxide, 15.1% by volume of methyl nitrite, 3.1% by volume of nitrogen monoxide, 13.2% by volume of methanol, 2.0% by volume of carbon dioxide and 46.9% by volume of nitrogen) was preheated to about 90° C. by a heat exchanger, and then introduced from the top of this catalyst layer by a diaphragm gas-recycling pump at a rate of 5.4 Nm³/hr., and the temperature of the central portion of the catalyst layer was maintained to be about 110° C. by circulating hot water to the shell side of the reactor.

The gas passed through the catalyst layer was led to the bottom of a Rasching ring packed gas-liquid contact type condenser A having an inside diameter of 158 mm and a height of 1,400 mm, and from the top of the condenser, methanol was introduced at a rate of 1.3 liters/hr., whereby the countercurrent contact was carried out at a temperature of 40° C. at the top and 43° C. at the bottom.

From the bottom of the condenser, there was obtained 2.2 kg./hr. of a condensed liquid (composition: 48.0% by weight of dimethyl oxalate, 1.5% by weight of dimethyl carbonate, 0.3% by weight of methyl oxalate and 48.0% by weight of methanol). On the other hand, from the top of the condenser, 5.0 Nm³/hr. of a non-condensed gas (composition: 13.3% by volume of carbon monoxide, 7.4% by volume of methyl nitrite, 11.9% by volume of nitrogen monoxide, 14.2% by volume of methanol, 2.4% by volume of carbon dioxide and 50.9% by volume of nitrogen) was obtained.

To this non-condensed gas, 119.0 liters/hr. of oxygen was mixed (the molar ratio of oxygen to nitrogen monoxide in the gas being 0.2) and the mixture was led to the bottom of the gas-liquid contact type regeneration column having an inner diameter of 158 mm and a height of 1,400 mm. From the top of the column, methanol was supplied at a rate of 5.0 liters/hr. (0.65 liter/hr. of which was supplied from the distillation column B mentioned below and 1.33 liters/hr. of which was supplied from the hydrolysis column mentioned below. The countercurrent contact was carried out at a temperature of 40° C. at the top of the column and 42° C. at the bottom of the column, whereby nitrogen oxide in the gas was generated into methyl nitrite. The regenerated gas from the regeneration column (composition: 13.0% by volume of carbon monoxide, 16.3% by volume of methyl nitrite, 3.4% by volume of nitrogen monoxide, 14.7% by volume of methanol, 2.3% by volume of carbon dioxide and 50.0% by volume of nitrogen), was supplied to and compressed by said gas recycling pump at a rate of 5.1 Nm³/hr. To 4.7 Nm³/hr. of the discharged gas, there was added 0.7 Nm³/hr. To 4.7 Nm³/hr. of the discharged gas, there was added 0.7 Nm³/hr. of a gaseous mixture containing 66.8% by volume of carbon monoxide, 6.3% by volume of methyl nitrite, 1.3% by volume of methanol, and 23.6% by volume of nitrogen, and the mixture was led to reactor A.

On the other hand, 4.2 liters/hr. of a methanol solution containing 5.0% by weight of water, withdrawn from the regeneration column, was subjected to distillation to remove water and the methanol thereby obtained was reused as a methanol source for said column.

To a distillation column A having an inside diameter of 30 mm and a height of 3,000 mm, 2.2 kg./hr. of the condensed liquid withdrawn from said condenser A was introduced and distilled at a temperature of 63° C. at the top and 166° C. at the bottom. From the bottom, 1.07 kg./hr. of a dimethyl oxalate liquid having a purity of 99.0% by weight was obtained. On the other hand, 0.74 Nm³/hr. of a gaseous distillate composed of 98.5% by volume of methanol, 1.13% by volume of dimethyl carbonate and 0.29% by volume of methyl formate, was obtained.

This gaseous distillate was led to a hydrolysis column having an inside diameter of 28.4 mm and a height of 1,000 mm [packed with 500 ml. of Neobead P (trade name) made by Mizusawa Kagaku Co.] and contacted with 17 g./hr. of steam at about 200° C., whereby dimethyl carbonate and methylformate in the gas were hydrolized and 1.33 liters/hr. of methanol was obtained and recycled to the above-mentioned regeneration column.

Mixed with 1.07 kg./hr. of dimethyl oxalate obtained from said distillation column A was 72.5 g./hr. of methyl glycolate obtained from the distillation column C mentioned below. The mixture was pressurized to 30 kg./cm²G., then mixed with a gas having the same pressure and composed of 83.2% by volume of hydrogen, and 14.0% by volume of nitrogen, and heated to about 200° C. The gaseous mixture thereby obtained was supplied to a reactor B having an inside diameter of 42.6 mm and a height of 2500 mm (packed with 3.0 liters of Cu-Cr-Ba series ST-203 catalyst made by Sakai Kagaku Co.).

The gas passed through the catalyst layer, was led to a condenser B having an inside diameter of 53.5 mm and a height of 1500 mm, and cooled to about 40° C. From the bottom, there was obtained 1.14 kg./hr. of a condensed liquid (composition: 43.9% by weight of ethylene glycol, 47.4% by weight of methanol, and 6.4% by weight of methyl glycolate). On the other hand, 9.2 Nm³/hr. of the noncondensed gas withdrawn from the top (composition: 83.7% by volume of hydrogen, and 15.5% by volume of nitrogen) was recycled as said hydrogen source.

To the distillation column B having an inside diameter of 30 mm and a height of 3000 mm, 1.14 kg./hr. of the condensed liquid obtained from the condenser B was led, and distillation was carried out at a temperature of 65° C. at the top and 158° C. at the bottom. The methanol distilled from the top was recycled to said regeneration column at a rate of 0.65 liter/hr. On the other hand, 0.59 kg./hr. of the distillation residue obtained from the bottom (composition: 84.7% by weight of ethylene glycol, and 12.2% by weight of methyl glycolate), was led to a distillation column C having an inside diameter of 30 mm and a height of 3000 mm, and distilled at a temperature of 95° C. at the top and 158° C. at the bottom. Recycled to said reactor B was 72.5 g./hr. of methyl glycolate distilled from the top. On the other hand, from the bottom, there was obtained 0.51 kg./hr. of ethylene glycol having a purity of 98.1% by weight, as the distillation residue.

EXAMPLE 5

In the tubes of a stainless multi-tubular reactor A, which has 8 tubes having an inside diameter of 28.0 mm and a height of 1,000 mm, there was packed 3.85 kg. (3.85 liters) of γ-alumina catalyst in a form of pellets having a diameter of 5 mm and a height of 3 mm and carrying 0.5% by weight of palladium.

A gaseous starting material compressed under 1.8 kg./cm² (gauge pressure) (composition: 20.0% by volume of carbon monoxide, 7.0% by volume of ethyl nitrite, 3.0% by volume of nitrogen monoxide, 6.0% by volume of ethanol, 3.2% by volume of carbon dioxide and 59.8% by volume of nitrogen) was preheated to about 90° C. by a heat exchanger and then introduced from the top of the catalyst layer by a diaphragm gas-recycling pump at a rate of 23.0 Nm²/hr., and the temperature of the central portion of the catalyst layer was maintained to be about 110° C. by circulating hot water to the shell side of the reactor.

The gas passed through the catalyst layer was led to the bottom of a Rasching ring packed gas-liquid contact condenser A having an inside diameter of 158 mm and a height of 1,400 mm, and from the top of the concenser, ethanol was introduced at a rate of 8.0 liters/hr., whereby the countercurrent contact was carried out at a temperature of 60° C. at the top and 63° C. at the bottom. From the bottom of the condenser, there was obtained 2.5 kg./hr. of a condensed liquid (composition: 54.7% by weight of diethyloxalate, 1.8% by weight of diethyl carbonate, 0.3% by weight of ethyl formate and 41.8% by weight of ethanol). On the other hand, from the top of the condenser 24.9 Nm³/hr. of a non-condensed gas (composition: 16.7% by volume of carbon monoxide, 4.6% by volume of ethyl nitrite, 4.6% by volume of nitrogen monoxide, 16.0% by volume of ethanol, 3.3% by volume of carbon dioxide and 54.0% by volume of nitrogen) was obtained.

To this non-condensed gas, 118.5 Nl./hr. of oxygen was mixed (the molar ratio of oxygen to nitrogen monoxide in the gaseous mixture being 0.104) and the mixture was led to the bottom of the gas-liquid contact type regeneration column having an inner diameter of 158 mm and a height of 1,400 mm. From the top of the column, ethanol is supplied at a rate of 2.3 liters/hr. (1.0 liter/hr. of which was supplied from the distillation column B mentioned below). The countercurrent contact was carried out at a temperature of 40° C. at the top of the column and 42° C. at the bottom of the column, whereby nitrogen monoxide in the gas was regenerated into ethyl nitrite. The regenerated gas from the regeneration column (composition: 18.4% by volume of carbon monoxide, 7.1% by volume of ethyl nitrite, 3.1% by volume of nitrogen monoxide, 6.2% by volume of ethanol, 3.3% by volume of carbon dioxide and 60.7% by volume of nitrogen), was supplied to and compressed by said gas recycling pump at a rate of 22.6 Nm³/hr. To 22.3 Nm³/hr. of the discharged gas, there was added 0.7 Nm³/hr. of gaseous mixture containing 71.5% by volume of carbon monoxide, 4.4% by volume of ethyl nitrite, 0.6% by volume of ethanol, and 23.6% by volume of nitrogen, and the mixture was led to the reactor A.

On the other hand, 8.9 liters/hr. of an ethanol solution containing 4.3% by weight of water, withdrawn from the regeneration column, was subjected to dehydration and then reused as an ethanol source for said column.

To a distillation column A having an inside diameter of 30 mm and a height of 3,000 mm, 2.5 kg./hr. of the condensed liquid withdrawn from said condenser A was introduced and distilled at a temperature of 78° C. at the top and 185° C. at the bottom. From the bottom, 1.38 kg./hr. of a diethyl oxalate liquid having a purity of 98.9% by weight was obtained. On the other hand, 0.52 Nm$^3$/hr. of a gaseous distillate composed of 97.8% by volume of ethanol, 1.7% by volume of diethyl carbonate and 0.5% by volume of ethyl formate, was obtained.

This gaseous distillate was led to a hydrolysis column having an inside diameter of 28.4 mm and a height of 1,000 mm [packed with 500 ml of Neobead P (trade name) made by Mizusawa Kagaku Co.] and contacted with 18.0 g./hr. of steam at about 200° C., whereby diethyl carbonate and ethyl formate in the gas were hydrolized and 1.33 liters/hr. of ethanol was obtained.

Mixed with 1.38 kg./hr. of diethyl oxalate obtained from said distillation column A was 75.0 g/hr. of ethyl glycolate obtained from the distillation column C mentioned below. The mixture was pressurized to 30 kg./cm$^2$G, then mixed with 11.0 Nm$^3$/hr a gas having the same pressure and composed of 85.0% by volume of hydrogen, and 14.0% by volume of nitrogen, and heated to about 200° C. The gaseous mixture thereby obtained was supplied to a reactor B having an inside diameter of 42.6 mm and a height of 2,500 mm (packed with 3.0 liters of Cu-Cr-Ba series St-203 catalyst made by Sakai Kagaku Co.).

The gas passed through the catalyst layer, was led to a condenser B having an inside diameter of 53.5 mm and a height of 1,500 mm, and cooled to about 40° C. From the bottom, there was obtained 1.5 kg./hr. of a condensed liquid (composition: 36.3% by weight of ethylene glycol, 56.0% by weight of ethanol, and 4.9% by weight of ethyl glycolate). On the other hand, 10.1 Nm$^3$/hr. of the noncondensed gas withdrawn from the top (composition: 83.8% by volume of hydrogen, and 15.5% by volume of nitrogen) was recycled as said hydrogen source.

To the distillation column B having an inside diameter of 30 mm and a height of 3.00% mm, 1.5 kg./hr. of the condensed liquid obtained from the condenser B was led, and distillation was carried out at a temperature of 78° C. at the top and 158° C. at the bottom. The ethanol distilled from the top was recycled to said regeneration column at a rate of 1.0 liter/hr. On the other hand, 0.64 kg./hr. of the distillation residue obtained from the bottom (composition: 85.0% by weight of ethylene glycol, and 12.2% by weight of ethyl glycolate), was led to a distillation column C having an inside diameter of 30 mm and a height of 3,000 mm, and distilled at a temperature of 69° C. at the top and 159° C. at the bottom. Recycled to said reactor B was 75 g./hr. of ethyl glycolate distilled from the top. On the other hand, from the bottom, there was obtained 0.56 kg./hr. of ethylene glycol having a purity of 98.0% by weight, as the distillation residue.

EXAMPLE 6

Mixed with 1.0 kg./hr. of dimethyl oxalate which had been obtained in the same manner as in Example 4 was 0.07 kg./hr. of methyl glycolate obtained from the distillation column C mentioned below. The mixture was pressurized to 30 kg./cm$^2$G., then mixed with a gas composed of 57.5% by volume of hydrogen, and 42.5% by volume of nitrogen under the same pressure, and heated to about 200° C. The gaseous mixture thereby obtained was supplied to a reactor having an inside diameter of 42.6 mm and a height of 2,500 mm (packed with 3.0 liters of Cu-Cr-Ba series ST-203 catalyst made by Sakai Kagaku Co.) at a rate of 30 Nm$^3$/hr.

The gas passed through the catalyst layer, was led to a condenser having an inside diameter of 53.5 mm and a height of 1,500 mm, and cooled to about 40° C. From the bottom, there was obtained 1.14 kg./hr. of a condensed liquid (composition: 43.9% by weight of ethylene glycol, 47.4% by weight of methanol, and 6.4% by weight of methyl glycolate). On the other hand, 28.7 Nm$^3$/hr. of the noncondensed gas withdrawn from the top (composition: 73.8% by volume of hydrogen, and 26.2% by volume of nitrogen) was recycled as said hydrogen source.

To the distillation column A having an inside diameter of 30 mm and a height of 3,000 mm, 1.14 kg./hr. of the condensed liquid obtained from the condenser was led, and distillation was carried out at a temperature of 65° C. at the top and 158° C. at the bottom. The methanol was distilled from the top at a rate of 0.54 kg./hr.

Led to a distillation column B having an inside diameter of 30 mm and a height of 3,000 mm, was 0.6 kg./hr. of the distillation residue withdrawn from the bottom of the distillation column A. Distillation was carried out at a temperature of 68° C. at the top and 160° C. at the bottom, whereby 0.02 kg./hr. of light-boiling substances (composition: 61.9% by weight of ethanol, 30.2% by weight of water and 7.9% by weight of methanol) was distilled out from the top.

Led to a distillation column C having an inside diameter of 30 mm and a height of 3,000 mm was 0.58 kg./hr. of the distillation residue withdrawn from the bottom of the distillation column B. Distillation was carried out at a temperature of 95° C. at the top and 158° C. at the bottom. Methyl glycolate distilled from the top in an amount of 0.07 kg./hr. was recycled to said reactor.

Led to a distillation column D having an inside diameter of 30 mm and a height of 3,000 mm was 0.51 kg./hr. of the distillation residue withdrawn from the bottom of the distillation column C. Distillation was carried out at a temperature of 119° C. at the top and 160° C. at the bottom. From the top, 0.49 kg./hr. of ethylene glycol having a purity of 100% was obtained. On the other hand, 0.02 kg./hr. of a high boiling substance as the distillation residue was discharged from the bottom out of the system.

EXAMPLE 7

Mixed with 1.37 kg./hr. of diethyl oxalate which had been obtained in the same manner as in Example 5 was 75 g./hr. of ethyl glycolate obtained from the distillation column C mentioned below. The mixture was pressurized to 30 kg./cm$^2$G., then mixed with 11.0 Nm$^3$/hr. of a gas composed of 85.0% by volume of hydrogen, and 14.0% by volume of nitrogen under the same pressure, and heated to about 200° C. The gaseous mixture thereby obtained was supplied to a reactor having an inside diameter of 42.6 mm and a height of 2,500 mm (packed with 3.0 liters of Cu-Cr-Ba series ST-203 catalyst made by Sakai Kagaku Co.).

The gas passed through the catalyst layer, was led to a condenser having an inside diameter of 53.5 mm and a height of 1,500 mm, and cooled to about 40° C. From the bottom, there was obtained 1.48 kg./hr. of a condensed liquid (composition: 36.3% by weight of ethylene glycol, 56.0% by weight of ethanol, and 4.9% by weight of ethyl glycolate). On the other hand, 10.1 Nm$^3$/hr. of the non-condensed gas withdrawn from the top (composition: 83.8% by volume of hydrogen, and 15.5% by volume of nitrogen) was recycled as said hydrogen source.

To the distillation column A having an inside diameter of 30 mm and a height of 3,000 mm, 1.48 kg./hr. of the condensed liquid obtained from the condenser was led, and distillation was carried out at a temperature of 78° C. at the top and 158° C. at the bottom. The ethanol was distilled from the top at a rate of 0.82 kg./hr.

Led to a distillation column B having an inside diameter of 30 mm and a height of 3,000 mm, was 0.66 kg./hr. of the distillation residue withdrawn from the bottom of the distillation column A. Distillation was carried out at a temperature of 78° C. at the top and 160° C. at the bottom. From the top, 0.02 kg./hr. of a light boiling substance (composition: 91.6% by weight) was distilled out.

Led to a distillation column C having an inside diameter of 30 mm and a height of 3,000 mm, was 0.64 kg./hr. of the distillation residue withdrawn from the bottom of the distillation column B. Distillation was carried out at a temperature of 117° C. at the top and 159° C. at the bottom. Ethyl glycolate distilled from the top at a rate of 75 g./hr. was recycled to said reactor.

Led to a distillation column D having an inside diameter of 30 mm and a height of 3,000 mm, was 0.56 kg./hr. of the distillation residue withdrawn from the bottom of the distillation column C. Distillation was carried out at a temperature of 119° C. at the top and 160° C. at the bottom. From the top, 0.54 kg./hr. of ethylene glycol having a purity of 100% was obtained. On the other hand, 0.02 kg./hr. of a high boiling substance, as the distillation residue, was discharged from the bottom out of the system.

We claim:

1. A process for continuously preparing ethylene glycol, which comprises
   (1) a first step of contacting a gas containing carbon monoxide and an ester of nitrous acid with a solid catalyst of platinum group metal series in the gaseous phase at a temperature of from 50° to 200° C. and a pressure of from ambient pressure to 10 kg/cm$^2$ (guage) thereby to obtain a product containing a diester of oxalic acid, and said ester of nitrous acid is an ester of a saturated monohydric aliphatic or alicyclic alcohol having 1 to 8 carbon atoms with nitrous acid,
   (2) a second step of condensing the product of the first step thereby to separate a non-condensed gas containing nitrogen monoxide formed by the catalytic reaction of the first step from a condensed liquid containing the diester of oxalic acid,
   (3) a third step of contacting in a regeneration column the non-condensed gas of the second step with a gas containing molecular oxygen and an alcohol to produce a gas mixture containing (i) an ester of nitrous acid and (ii) nitrogen monoxide and controlling the concentration of said nitrogen monoxide within the range of from 2 to 7% by volume, and recycling said gas mixture containing an ester of nitrous acid to the first step,
   (4) a fourth step of contacting the condensed liquid of the second step containing the diester of oxalic acid and hydrogen with a catalyst for hydrogenation in the gaseous phase thereby to obtain a product containing ethylene glycol,
   (5) a fifth step of distilling the product of the fourth step thereby to distil out the alcohol and to obtain ethylene glycol, and
   (6) a sixth step of recycling the alcohol of the fifth step as an alcohol source for the third step.

2. The process of claim 1, wherein said solid catalyst comprises palladium or a salt thereof.

3. The process of claim 1, wherein said catalytic reaction is conducted at a temperature of 80° to 150° C.

4. The process of claim 1, wherein the product of the first step is cooled for condensation at a temperature of at most the boiling point of an alcohol while contacting it with an alcohol.

5. The process of claim 4, wherein said alcohol is a lower alcohol having 1 to 4 carbon atoms.

6. The process of claim 1, wherein the amount of said gas containing molecular oxygen in the third step is in the range of 0.08 to 0.2 mole in terms of oxygen relative to one mole of nitrogen monoxide introduced into said regeneration column.

7. The process as claimed in any one of claims 1, 2, 3, 4, 5 or 6, wherein the amount of the alcohol used in the third step is in the range of 2 to 5 parts by volume relative to one part by volume of nitrogen monoxide introduced into said regeneration column.

8. The process of claim 1, wherein, prior to the fourth step, the condensed liquid of the second step is evaporated to distil out the alcohol containing the diester of carbonic acid by-produced in the catalytic reaction of the first step and to obtain the diester of oxalic acid as a distillation residue.

9. A process for continuously preparing ethylene glycol, which comprises
   (1) a first step of contacting a gas containing carbon monoxide and an ester of nitrous acid with a solid catalyst of platinum group metal series in the gaseous phase at a temperature of from 50° to 200° C. and a pressure of from ambient pressure to 10 kg/cm$^2$ (guage) thereby to obtain a product containing a diester of oxalic acid, and said ester of nitrous acid is an ester of a saturated monohydric aliphatic or alicyclic alcohol having 1 to 8 carbon atoms with nitrous acid,
   (2) a second step of condensing the product of the first step thereby to separate a non-condensed gas containing nitrogen monoxide formed by the catalytic reaction of the first step from a condensed liquid containing the diester of oxalic acid, and then evaporating the thus condensed liquid to distil out the alcohol containing the diester of carbonic acid by-produced in the catalytic reaction of the first step and to obtain the diester of oxalic acid as a distillation residue,
   (3) a third step of contacting in a regeneration column the non-condensed gas of the second step with a gas containing molecular oxygen and an alcohol to produce a gas mixture containing (i) an ester of nitrous acid and (ii) nitrogen monoxide and controlling the concentration of said nitrogen monoxide within the range of from 2 to 7% by volume, and recycling the resulting gas containing an ester of nitrous acid to the first step, (4) a fourth step of contacting the distillation residue of the second step containing the diester of oxalic acid and hydrogen with a catalyst for hydrogenation in the gaseous phase thereby to obtain a product containing ethylene glycol, (5) a fifth step of distilling the product of the fourth step thereby to distil out the alcohol and to obtain ethylene glycol, and (6) a sixth step of recycling the alcohol of the fifth step as an alcohol source for the third step.

10. The process of claim 9, wherein the alcohol of the second step is introduced in a hydrolysis column thereby hydrolyzing the diester of carbonic acid and recycling the alcohol thereby obtained, as an alcohol source for the third step.

11. The process of claim 10, wherein the hydrolysis is carried out by a gas phase reaction in the presence of an alumina catalyst at a temperature of from 150° to 250° C.

12. The process of claim 1 or 9, wherein the glycolic acid formed in the fourth step as a by-product is distilled out in the fifth step and then recycled to the fourth step.

13. A process for continuously preparing ethylene glycol, which comprises (1) a first step of contacting a gas containing carbon monoxide and an ester of nitrous acid with a solid catalyst of platinum group metal series in the gaseous phase at a temperature of from 50° to 200° C. and a pressure of from ambient pressure to 10 kg/cm² (guage) thereby to obtain a product containing a diester of oxalic acid, and said ester of nitrous acid is an ester of a saturated monohydric aliphatic or alicyclic alcohol having 1 to 8 carbon atoms with nitrous acid, (2) a second step of condensing the product of the first step thereby to separate a non-condensed gas containing nitrogen monoxide formed by the catalytic reaction of the first step from a condensed liquid containing the diester of oxalic acid, (3) a third step of contacting in a regeneration column the non-condensed gas of the second step with a gas containing molecular oxygen and an alcohol to produce a gas mixture containing (i) an ester of nitrous acid and (ii) nitrogen monoxide and controlling the concentration of said nitrogen monoxide within the range of from 2 to 7% by volume, and recycling the resulting gas containing an ester of nitrous acid to the first step, (4) a fourth step of contacting the condensed liquid of the second step containing the diester of oxalic acid and hydrogen with a catalyst for hydrogenation in the gaseous phase thereby to obtain a product containing ethylene glycol, ester of glycolic acid and the alcohol, (5) a fifth step of distilling the product of the fourth step thereby to distil out the alcohol and the glycolic acid formed in the fourth step and to obtain ethylene glycol, and then recycling the glycolic acid to the fourth step, and (6) a sixth step of recycling the alcohol of the fifth step as an alcohol source for the third step.

14. The process of claim 13, wherein the distillation residue containing ethylene glycol and obtained by the distillation of the glycolic acid in the fifth step is subjected further to distillation to obtain ethylene glycol of high purity.

15. The process of claim 1, 9 or 13, wherein, prior to the fifth step, the product is condensed to separate a non-condensed gas containing hydrogen and a condensed liquid containing ethylene glycol, and the condensed liquid is distilled to obtain ethylene glycol, while recycling the non-condensed gas as a hydrogen source for the fourth step.

16. The process of claim 1, 9 or 13, wherein in said first step, said solid catalyst comprises palladium or a salt thereof, said reaction is carried out at a temperature of 80° to 150° C.; wherein the product of the first step is cooled for condensation at a temperature of at most the boiling point of an alcohol while contacting it with an alcohol; and wherein in said third step, said alcohol is a saturated monohydric aliphatic or cycloaliphatic alcohol having 1 to 8 carbon atoms and the amount of said alcohol is in the range of 2 to 5 parts by volume relative to 1 part by volume of nitrogen monoxide introduced into said regeneration column and the amount of said gas containing molecular oxygen is between 0.08 and 0.2 mole in terms of oxygen relative to 1 mole of nitrogen monoxide introduced to said regeneration column; and wherein the concentration of nitrogen monoxide in the gas withdrawn from the regeneration column is within the range of from 2 to 7 percent by volume.

* * * * *